(12) United States Patent
Schreiber et al.

(10) Patent No.: US 9,089,557 B2
(45) Date of Patent: Jul. 28, 2015

(54) **HUMAN ANTIBODIES AGAINST *PSEUDOMONAS AERUGINOSA* LPS DERIVED FROM TRANSGENIC XENOMOUSE**

(71) Applicant: CASE WESTERN RESERVE UNIVERSITY, Cleveland, OH (US)

(72) Inventors: John R. Schreiber, Sudbury, MA (US); Kulwant Kamboj Kaur, Maple Grove, MN (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 14/636,753

(22) Filed: Mar. 3, 2015

(65) Prior Publication Data

US 2015/0175680 A1 Jun. 25, 2015

Related U.S. Application Data

(63) Continuation of application No. 13/118,074, filed on May 27, 2011, now Pat. No. 8,986,990, which is a continuation of application No. 10/380,092, filed as application No. PCT/US01/28019 on Sep. 7, 2001, now Pat. No. 7,972,845.

(60) Provisional application No. 60/259,472, filed on Jan. 3, 2001, provisional application No. 60/230,640, filed on Sep. 7, 2000.

(51) Int. Cl.
*A61K 39/40* (2006.01)
*A61K 45/06* (2006.01)
*C07K 16/12* (2006.01)
*G01N 33/92* (2006.01)
*C12N 15/85* (2006.01)

(52) U.S. Cl.
CPC ............ *A61K 39/40* (2013.01); *C12N 15/8509* (2013.01)

(58) Field of Classification Search
None
See application file for complete search history.

*Primary Examiner* — Robert A Zeman
(74) *Attorney, Agent, or Firm* — Hahn Loeser & Parks LLP

(57) ABSTRACT

The invention described herein provides for human antibodies produced in non-human animals that specifically bind to *Pseudomonas aeruginosa* Lipopolysaccharide (LPS). The invention further provides methods for making the antibodies in a non-human animal, expression of the antibodies in cell lines including hybridomas and recombinant host cell systems. Also provided are kits and pharmaceutical compositions comprising the antibodies and methods of treating or preventing *pseudomonas* infection by administering to a patient the pharmaceutical compositions described herein.

2 Claims, 10 Drawing Sheets

Figure 1: S20 Monoclonal Antibody Gene Usage

Heavy Chain Gene Segments

| VH | D | JH |
|---|---|---|
| $V_H3/V3\text{-}33$ | D2-8 | $J_H4b$ |

Light Chain Gene Segments

| VL | JL |
|---|---|
| $V_\kappa 2/A2$ | $J_\kappa 1$ |

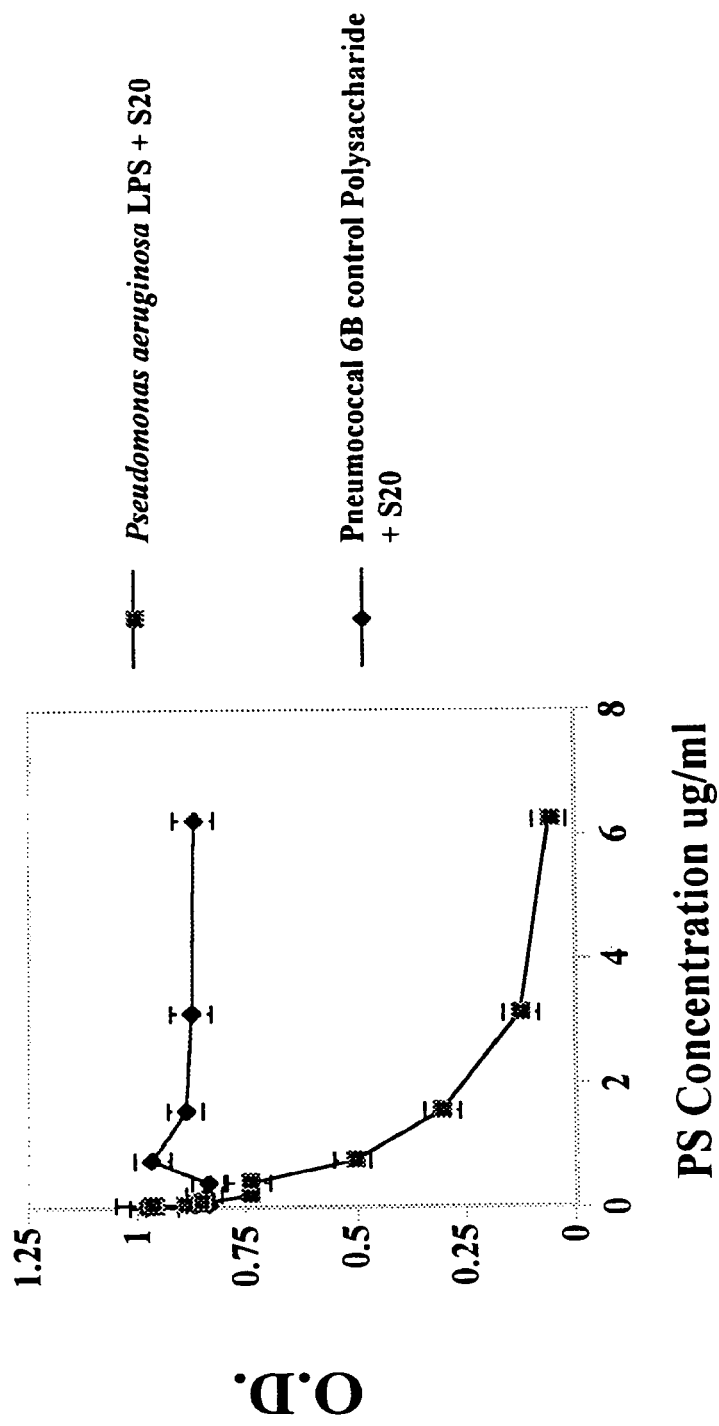
Figure 2: S20 Monoclonal Antibody Specifically Binds Solid Phase *Pseudomonas aeruginosa* LPS

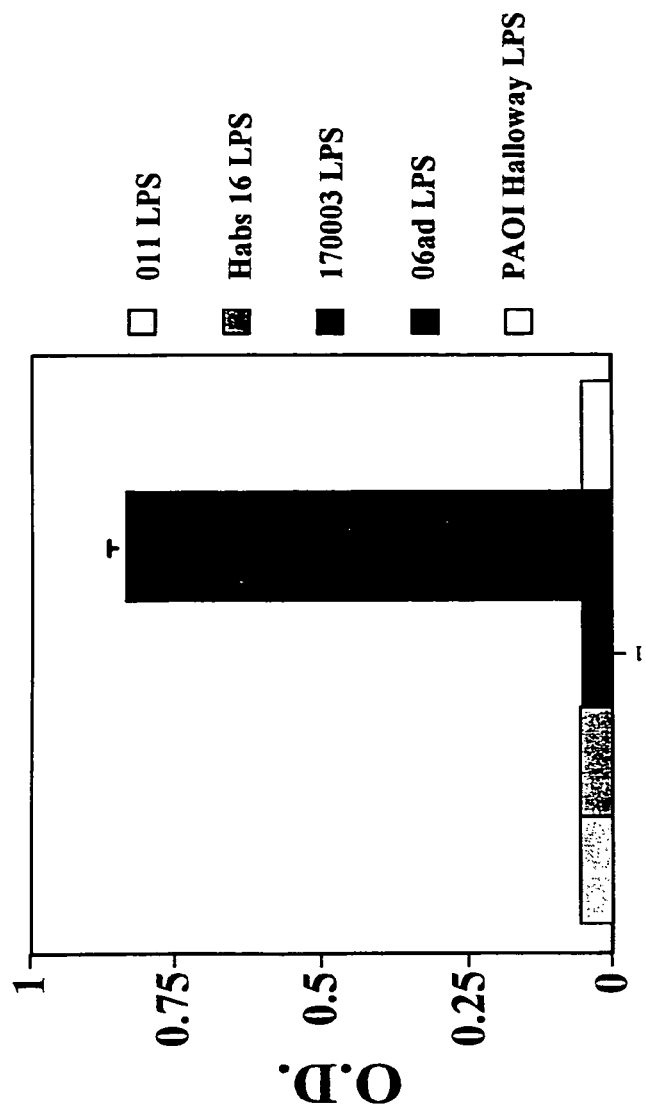
Figure 3: S20 Monoclonal Antibody Specifically Binds *Pseudomonas aeruginosa* O6ad LPS

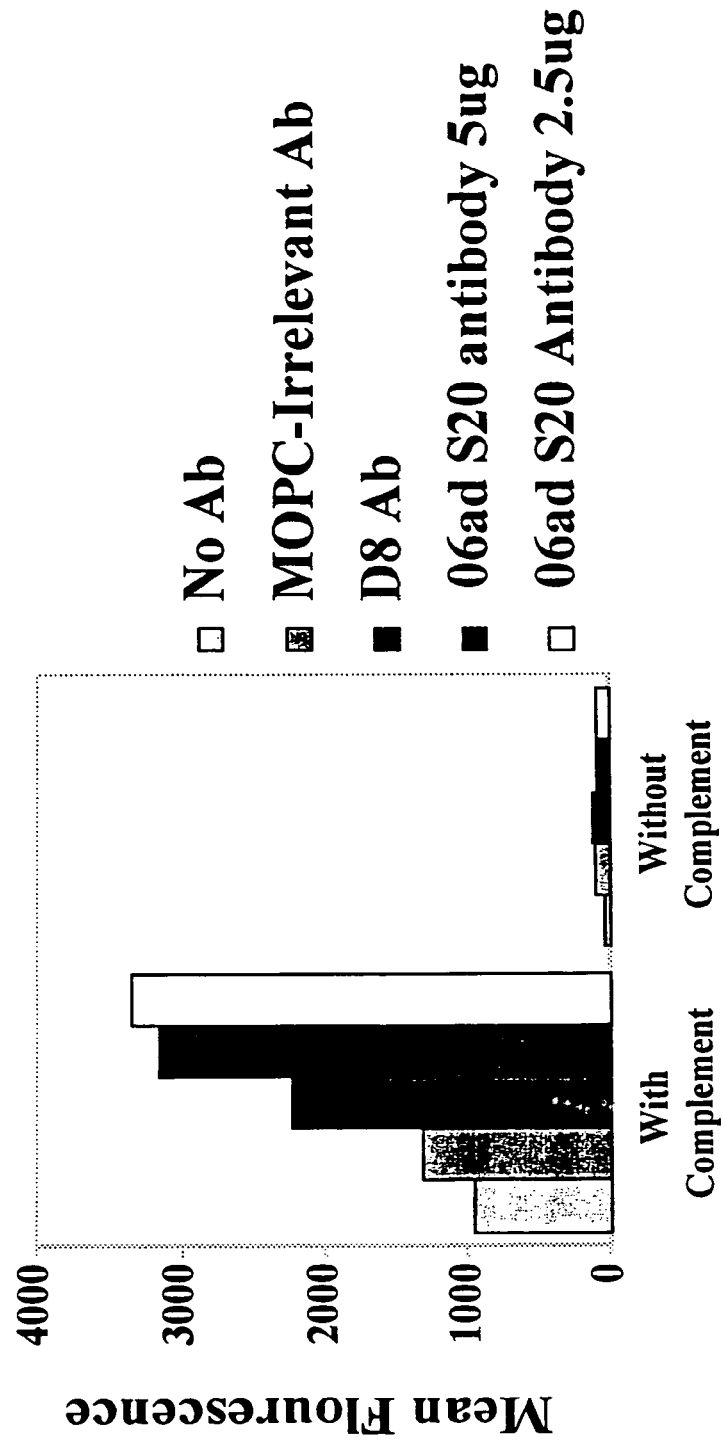
Figure 4: S20 Monoclonal Antibody Opsonization Promotes Complement-Dependent Phagocytosis

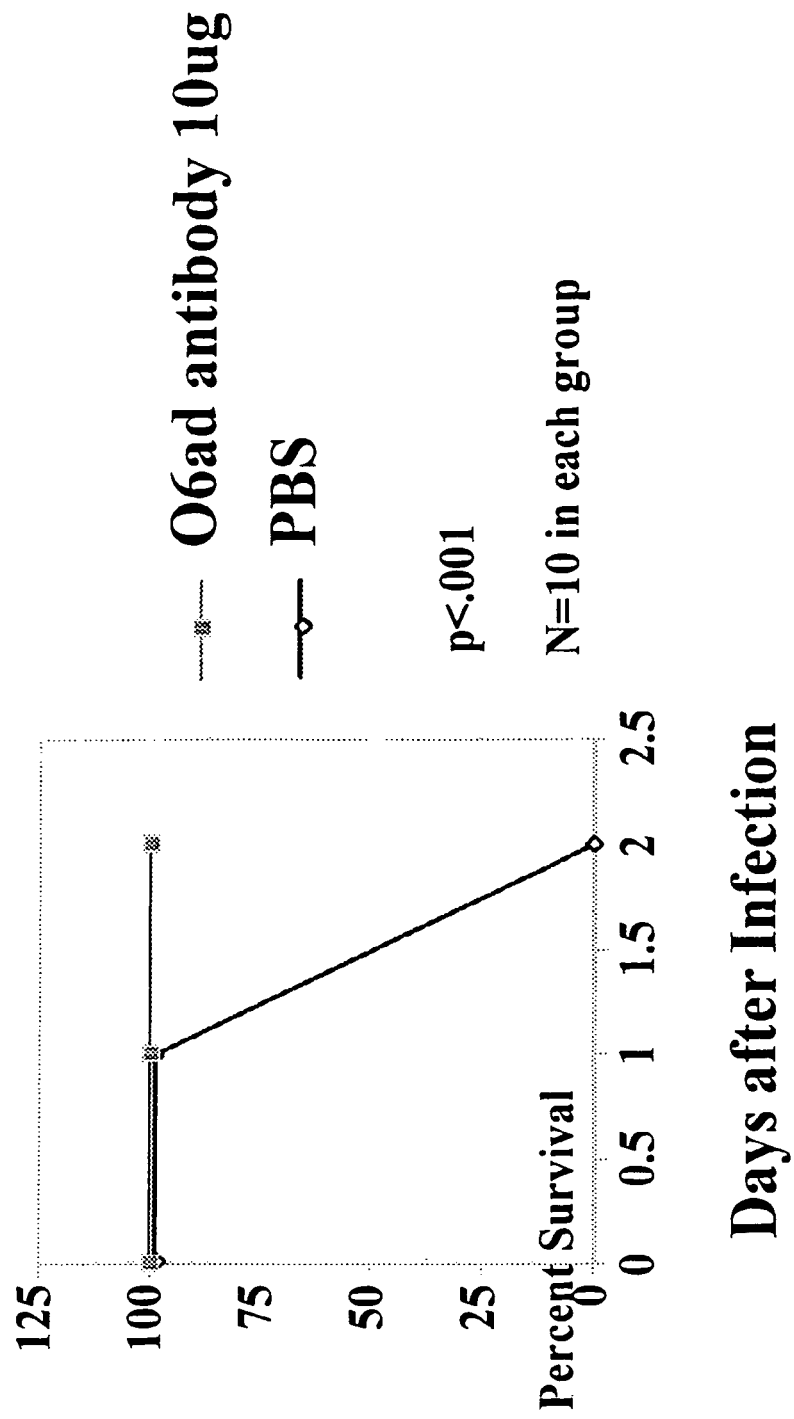
Figure 5: S20 Monoclonal Antibody Protects Neutropenic Mice From Fatal *Pseudomonas aeruginosa* Sepsis Heavy Chain Variable Region Sequence (SEQ ID:1)

CAGGTGCAGCTGGTGGAGTCTGGGGGAGGCGTGGTCCAGCCTGGGAGGTCCCTGAGACTC
TCCTGTGCAGCGTCTGGATTCACCTTCAGTAGCTATGGCATCGACTGGGTCCGCCAGGCT
CCAGGCAAGGGGCTGGAGTGGGTCGGACGTATATGGTATAGTGGAAGTAATAAATACTAT
GCAGACTCCGTGAAGGGCCGATTCACCATCTCCAGAGACAATTCCAAGAACACGCTGTAT
CTGCAAATGAACAGCCTGAGAGCCGAGGACACGGCTGTGTATTACTGTGCGAGAGATCCC
CACTATACCCGGGGTTTTGACTACTGGGGCAAGGGAACCCTGGTCACCGTCTCCTCAGCC
TCCACCAAAGGGCCCATCGGTCTTCCCCTGGCGCCCTGCTCCAGGAGCACCTCCGAGAGC
ACAGCGGCCCTGGGCTGCCTGGTCAAGGACTACTTCGCCGAA

Heavy Chain Variable Region Sequence (SEQ ID:2)

QVQLVESGGGVVQPGRSLRLSCAASGFTFSSYGIDWVRQAPGKGLEWVGRIWYSGSNKYY
ADSVKGRFTISRDNSKNTLYLQMNSLRAEDTAVYYCARDPHYTRGFDYWGKGTLVTVSSA
STKGPIGLPLAPCSRSTSESTAALGCLVKDYFAE

Light Chain Variable Region Sequence (SEQ ID:3)

GATGTTGTGATGACCCAGACTCCACTCTCTCTGTCCGTCACCCCTGGACAGCCGGCCTCC
ATCTCCTGCAGGTCTAGTCAGAGCCTCCTGCATAGTGATGGAATGACCTATTTTTCTTGG
TATTTGCAGAAGCCAGGCCAGCCTCCACAGCTCCTGATCTATGAAGTTTCCAACCGGTTC
TCTGGAGTGCCAGATAGGTTCAGTGGCAGCGGGTCAGGGACAGATTTCACACTGAAAATC
AGCCGGGTGGAGGCTGAGGATGTTGGGGTTTATTACTGCATGCAAAATATACAGCTTCCG
TGGACGTTCGGCCAAGGGACCAAGGTGGAAATCAAACGAACTGTGGCTGCACCATCTGTC
TTCATCTTCCCGCCATCTGAT

Light Chain Variable Region Sequence (SEQ ID:4)

DVVMTQTPLSLSVTPGQPASISCRSSQSLLHSDGMTYFSWYLQKPGQPPQLLIYEVSNRF
SGVPDRFSGSGSGTDFTLKISRVEAEDVGVYYCMQNIQLPWTFGQGTKVEIKRTVAAPSV
FIFPPSD

FIGURE 6

Heavy Chain Variable Region Sequence

Framework 1
CAGGTGCAGCTGGTGGAGTCTGGGGGAGGCGTGGTCCAGCCTGGGAGGTCC
 Q  V  Q  L  V  E  S  G  G  V  V  Q  P  G  R  S CDR 1
CTGAGACTCTCCTGTGCAGCGTCTGGATTCACCTTCAGT<u>AGCTATGGCATG</u>
 L  R  L  S  C  A  A  S  G  F  T  F  S  <u>S  Y  G  M</u>

Framework 2                                        CDR2
<u>CA</u>CTGGGTCCGCCAGGCTCCAGGCAAGGGGCTGGAGTGGGTGGCA<u>GCT</u>
 <u>H</u>  W  V  R  Q  A  P  G  K  G  L  E  W  V  A  <u>A</u>

<u>ATATGGTATAGTGGAAGTAATAAATACTATGCAGACTCCGTGAAGGGCCGA</u>
 <u>I  W  Y  S  G  S  N  K  Y  Y  A  D  S  V  K  G</u>  R

Framework 3
TTCACCATCTCCAGAGACAATTCCAAGAACACGCTGTATCTGCAAATGAAC
 F  T  I  S  R  D  N  S  K  N  T  L  Y  L  Q  M  N CDR3
AGCCTGAGAGCCGAGGACACGGCTGTGTATTACTGTGCGAGA<u>GATCCCCAC</u>
 S  L  R  A  E  D  T  A  V  Y  Y  C  A  R  <u>D  P  H</u>

Framework 4
<u>TATACCCGGGGTTTTGACTAC</u>TGGGGCAAGGGAACCCTGGTCACCGTCTCC
 <u>Y  T  R  G  F  D  Y</u>  W  G  K  G  T  L  V  T  V  S Constant
TCA<u>GCCTCCACCAAAGGGCCCATCGGTCTTCCCCTGGCGCCCTGCTCCAGG</u>
 S  A  S  T  K  G  P  I  G  L  P  L  A  P  C  S  R AGCACCTCCGAGAGCACAGCGGCCCTGGGCTGCCTGGTCAAGGACTACTTC
 S  T  S  E  S  T  A  A  L  G  C  L  V  K  D  Y  F

GCCGAA
 A  E

Figure 9

Light Chain Variable Region Sequence

Framework 1
GATGTTGTGATGACCCAGACTCCACTCTCTCTGTCCGTCACCCCTGGACAG
 D   V   V   M   T   Q   T   P   L   S   L   S   V   T   P   G   Q

CDR 1
CCGGCCTCCATCTCCTGCAGGTCTAGTCAGAGCCTCCTGCATAGTGATGGA
 P   A   S   I   S   C   R   S   S   Q   S   L   L   H   S   D   G

Framework 2
ATGACCTATTTTTCTTGGTATTTGCAGAAGCCAGGCCAGCCTCCACAGCTC
 M   T   Y   F   S   W   Y   L   Q   K   P   G   Q   P   P   Q   L

CDR 2         Framework 3
CTGATCTATGAAGTTTCCAACCGGTTCTCTGGAGTGCCAGATAGGTTCAGT
 L   I   Y   E   V   S   N   R   F   S   G   V   P   D   R   F   S GGCAGCGGGTCAGGGACAGATTTCACACTGAAAATCAGCCGGGTGGAG
 G   S   G   S   G   T   D   F   T   L   K   I   S   R   V   E

CDR 3
GCTGAGGATGTTGGGGTTTATTACTGCATGCAAAATATACAGCTTCCG
 A   E   D   V   G   V   Y   Y   C   M   Q   N   I   Q   L   P

Framework 4                  Constant
TGGACGTTCGGCCAAGGGACCAAGGTGGAAATCAAACGAACTGTGGCT
 W   T   F   G   Q   G   T   K   V   E   I   K   R   T   V   A

GCACCATCTGTCTTCATCTTCCCGCCATCTGAT
 A   P   S   V   F   I   F   P   P   S   D

Figure 10

HUMAN ANTIBODIES AGAINST *PSEUDOMONAS AERUGINOSA* LPS DERIVED FROM TRANSGENIC XENOMOUSE

CROSS REFERENCED TO RELATED APPLICATIONS

This application is a continuation of U.S. application Ser. No. 13/118,074, now U.S. Pat. No. 8,986,990, filed May 27, 2011, which is a continuation of U.S. application Ser. No. 10/380,092, now U.S. Pat. No. 7,972,845, filed Sep. 7, 2001, which is a national stage entry of international application number PCT/US2001/028019, filed Sep. 7, 2001, which claims priority from U.S. provisional application Nos. 60/259,472, filed Jan. 3, 2001, and 60/230,640, filed Sep. 7, 2000, which are incorporated by reference herein.

TECHNICAL FIELD OF THE INVENTION

The present invention relates to compositions and methods for treating or preventing *Pseudomonas aeruginosa* infection and conditions caused by such infection. Specifically, the present invention relates to human antibodies that specifically bind to *Pseudomonas aeruginosa* Lipopolysaccharide (LPS) and encoding nucleic acid molecules thereof. The invention further relates to methods for making the antibodies in a non-human animal and expressing the antibodies in cell lines including hybridomas and recombinant host cell systems. The invention also relates to kits and pharmaceutical compositions comprising the antibodies. The invention further relates to methods of treating or preventing *Pseudomonas* infection by administering to a patient any of the compositions described herein.

BACKGROUND OF THE INVENTION

*Pseudomonas aeruginosa* Infections

*Pseudomonas aeruginosa* are Gram-negative, flagellated rod bacteria that continue to be a significant pathogen in nosocomial infections resulting from surgery, prosthesis implantation and respiratory tract procedures. *Pseudomonas aeruginosa* also is an opportunistic pathogen in the etiology of cancer, cystic fibrosis, diabetes, heart disease, otitis externa (swimmer's ear), osteomyelitis, corneal ulcers, folliculitis, mastitis, pneumonia, meningitis, urinary tract infections, endocarditis, peritonitis and other diseases found in geriatric or immunocompromised patients.

Surgical patients are often at increased risk of *Pseudomonas aeruginosa* infection by virtue of their illness (e.g., trauma, burns, inhalation injury and cancer) or treatment (e.g., disruption of natural epithelial barriers by incision or percutaneous catheterization, endotracheal intubation, cardiac and thoracic surgery, neurosurgery, and gastrointestinal surgery). Disruption of natural intestinal flora by antibiotic treatments or prophylaxis, therapeutic immunosuppression of solid organ transplant recipients, or environmental exposure to *Pseudomonas aeruginosa* can place patients at increased risk. Moreover, multi-drug-resistant strains can cause significant infections in inpatient units as well as nursing homes.

Surgical patients are affected by nosocomial pneumonia, often caused by *Pseudomonas aeruginosa*. Onset occurs after the first 72 hours of hospitalization and is characterized by fever, purulent sputum, leukocytosis and a new or changed lung infiltrate revealed by chest radiography. The oropharynx is colonized rapidly, which may spread into the lower respiratory tract. Incidence of nosocomial infection in surgical patients overall is approximately 5% to 8%, and is probably higher in all critically ill patients. The incidence of pneumonia reported from surgical intensive care units (ICUs) is 15% to 20%, and occasionally higher. See Barie et al. *Am. J. Surgery* 179:2S-7S (2000).

Cystic fibrosis (CF) patients suffer chronic colonization with a narrow but evolving spectrum of bacterial pathogens *Pseudomonas aeruginosa* remains the major CF pathogen with a worldwide prevalance of up to 80% to 90% in CF adults. Such infections lead to intermittent episodes of debilitating inflammatory exacerbations and progressive lung damage. Emerging pathogens also tend to be resistant to multiple antibiotic regimens, thus infection control plays a critical role in the quality of life and life expectancy of CF patients.

The onset of chronic colonization is associated with acceleration of forced expiratory volume (FEV). The original colonizing strain transforms into a mucoid colonial form which is due to copious production of a highly viscid exopolysaccharide known as alginate. The colonizing strain becomes significantly more mucinophilic and chemotactic and is associated with impaired mucociliary clearance. See Govan *J. Royal Soc. Med.* 93 Supp. 38:40-45 (2000). Moreover, the *Pseudomonas aeruginosa* isolated from lungs of CF patients show changes in the LPS fatty acid acylation pattern and enhanced resistance to the bactericidal activity of some cationic antimicrobial peptides (CAMPs).

Alterations in *Pseudomonas aeruginosa* LPS lipid A were found in CF isolates that increased both bacterial resistance to antimicrobial peptides and the ability of LPS to elicit inflammatory mediators. CF patients have very high antibody titers to *Pseudomonas aeruginosa* LPS in both serum and sputum, which might neutralize its biological activities in vivo (e.g. proinflammatory mediator release). See Pier *Trends Micriobiol.* 8:247-251 (2000).

The leading cause of morbidity and mortality in severe burn wounds patients is infection with *Pseudomonas aeruginosa*, See Lee et al. *Vaccine* 18:1952-1961 (2000). Burn wounds are highly exudative, creating a moist, nutrient-rich environment for bacterial colonization. Burn wounds are largely inaccessible to the patient's immune responses and vascularly-delivered antibiotics due to the severe tissue injury. Moreover, burn wounds leave the host immunocompromised with endogenously decreased levels of immunoglobulin gamma (IgG). Without treatment, burn wound infections can spread and develop into sepsis with the associated production of inflammatory cytokines, including interleukin-1 (IL-1), IL-6, and tumor necrosis factors (TNFs). Burn wound infections may also result in delayed healing, increased scarring, conversion of a partial thickness defect to a full thickness defect and increased nutritional demands.

Intravenous immunoglobulin (IVIG) has been used increasingly to treat both bacterial and viral infections and primary and secondary immunodeficiency disorders. WIG is comprised of pooled human polyclonal antibodies from normal donors which are used as a substitution therapy for primary and secondary antibody deficiencies and to treat immune-mediated diseases, including autoimmune and systemic inflammatory conditions. Immunoglobulins promote the opsonization and phagocytosis of bacteria, neutralization of bacterial toxins, inhibition of microbial attachment, and the complement-induced lysis of bacteria. See Felts et al. *Burns* 25:415-423 (1999).

Direct and local delivery of protective immunoglobulins to wound and burn sites represents a rational means to overcome the lack of vascularization of burn wounds as well as biofilm barriers. Local delivery of IgG, both prophylactically and post-infection, was demonstrated to improve survival in mouse models of *Pseudomonas aeruginosa* infected burn wounds. See Felts et al. *Burns* 25:415-423 (1999).

Advances in the bioengineering of prosthetic devices has improved the lives of millions of patients. However, this progress has been tempered by implant-associated infections that often resist antibiotic treatment. Infectious organisms, including *Pseudomonas aeruginosa*, preferentially target synthetic implanted materials, eliciting serious and costly infections that frequently require removal of the colonized device.

Initial microbial adhesion is a primary determinant of biomaterial colonization because initially adhering microorganisms often progress to a mature biofilm attached to the biomaterial surface. The focus of research aimed at reducing biofilm formation on prostheses has been directed toward modifying or coating the surface of the implanted materials. Approaches utilizing surface chemistry and antibiotic-releasing coatings, however, have not been fully successful.

Because surgical sites are often immunocompromised, a promising approach involves the immunostimulation of the local wound site. Studies have shown that pooled polyclonal human antibodies opsonize infecting bacteria, and pooled antibodies can inhibit *Pseudomonas aeruginosa* adhesion rates and surface-growth dynamics, thus reducing biofilm formation. See Poelstra et al. *J. Biomed. Mat. Res.* 51:224-232 (2000).

Peritonitis is often caused by ulcers, appendicitis, diverticulitis, ileus, gunshot or stab wounds, disturbances during abdominal surgery, and continuous ambulatory peritoneal dialysis (CAPD). Nosocomial peritonitis, caused by exogenous pathogenic bacteria including *Pseudomonas aeruginosa*, is an especially acute problem for immunocompromised and geriatric populations.

Current treatment regimens for peritonitis focus on antibiotics, however, antibiotic resistance occurs at a significant rate and is frequently associated with clinical failure. IVIG has shown promising but inconsistent results in peritonitis, however, as with burn wounds, local (peritoneal) delivery of pooled polyclonal immunoglobulin against *Pseudomonas aeruginosa* was shown to significantly reduce infection in a mouse model. See Barekzi et al. *Antimicrob. Agents Chemotherap.* 43:1609-1615 (1999).

Treating *Pseudomonas aeruginosa* infections with antibiotic regimens has become increasingly difficult because, inter alia, antibiotic resistant strains have arisen. The emergence of passive antibody therapy for the prevention and treatment of *Pseudomonas aeruginosa* infections, though promising, has been tempered by the availability purified human antibodies, free of non-human animal antibodies, that bind specifically to *Pseudomonas aeruginosa* in clinical quantities.

Non-human antibody preparations, including murine monoclonal antibodies, are not generally acceptable for human therapies because of their immunogenicity. Human polyclonal antibody preparations, although suitable for human therapies, have variable titers of protective antibodies for *Pseudomonas aeruginosa* and a high cost of purifying antibodies from multiple donors.

Monoclonal antibodies theoretically can be made in unlimited quantity, at a low cost and with a desired specificity. However, efficacious human monoclonal antibodies are difficult to make and require human B cells expressing appropriate antibodies to be transformed with Epstein-Ban virus. The resulting monoclonal antibody preparations would not likely be appropriate for human therapeutic use. Moreover, most of the human monoclonal antibodies tested to date have been IgM which penetrate poorly into pulmonary tissue and can be associated with immune complex formation and enhanced inflammation.

Therefore, there is a need for purified human IgG antibodies that bind specifically to *Pseudomonas aeruginosa*, methods for its preparation and use, and pharmaceutical compositions and kits thereof.

SUMMARY OF THE INVENTION

The present invention provides isolated human antibodies that specifically bind to *Pseudomonas aeruginosa* Lipopolysaccharide (LPS). The invention further provides methods for making the antibodies in a non-human animal, expression of the antibodies in cell lines including hybridomas and recombinant host cell systems. The invention also provides kits and pharmaceutical compositions comprising the antibodies. Moreover, the invention provides methods of treating or preventing *pseudomonas* infection by administering to a patient the pharmaceutical compositions described herein.

BRIEF DESCRIPTION OF THE DRAWINGS

FIG. 1 shows the human immunoglobulin variable (V), diversity (D) and joining (J) regions utilized by the hybridoma that produces the S20 monoclonal anti-*Pseudomonas aeruginosa* antibody.

FIG. 2 depicts binding inhibition assays that show the S20 human monoclonal antibody binding with specificity to the *Pseudomonas aeruginosa* LPS. Soluble *Pseudomonas aeruginosa* LPS, but not soluble Pneumococcal 6B control polysaccharide, was able to inhibit S20 binding to solid phase *Pseudomonas aeruginosa* LPS.

FIG. 3 shows that the S20 monoclonal antibody specifically binds the *Pseudomonas aeruginosa* 06ad serotype LPS but does not bind solid phase LPS derived from the 011, Habs 16, 170003 and PAOI Halloway strains.

FIG. 4 shows that S20 opsonization promotes complement-dependent phagocytosis. Flow cytometry analysis of peripheral nuclear monocytes (PMNs) showed that the PMNs phagocytosed FITC labeled, opsonized *Pseudomonas aeruginosa* only in the presence of complement.

FIG. 5 shows that the S20 monoclonal antibody protected neutropenic mice from fatal *Pseudomonas aeruginosa* sepsis.

FIG. 6 sets forth the DNA and amino acid sequences of the heavy chain and light chain variable regions of human monoclonal antibody S20 (IgG).

FIG. 9 indicates the location of CDRs 1-3 of the heavy chain variable region of the S20 human monoclonal antibody. The nucleic acid sequence shown corresponds to SEQ ID NO:1. The amino acid sequence shown corresponds to SEQ ID NO:2.

FIG. 10 indicates the location of CDRs 1-3 of the kappa light chain variable region of the S20 human monoclonal antibody. The nucleic acid sequence shown corresponds to SEQ ID NO:3. The amino acid sequence shown corresponds to SEQ ID NO:4.

DETAILED DESCRIPTION OF THE INVENTION

Figure 7:
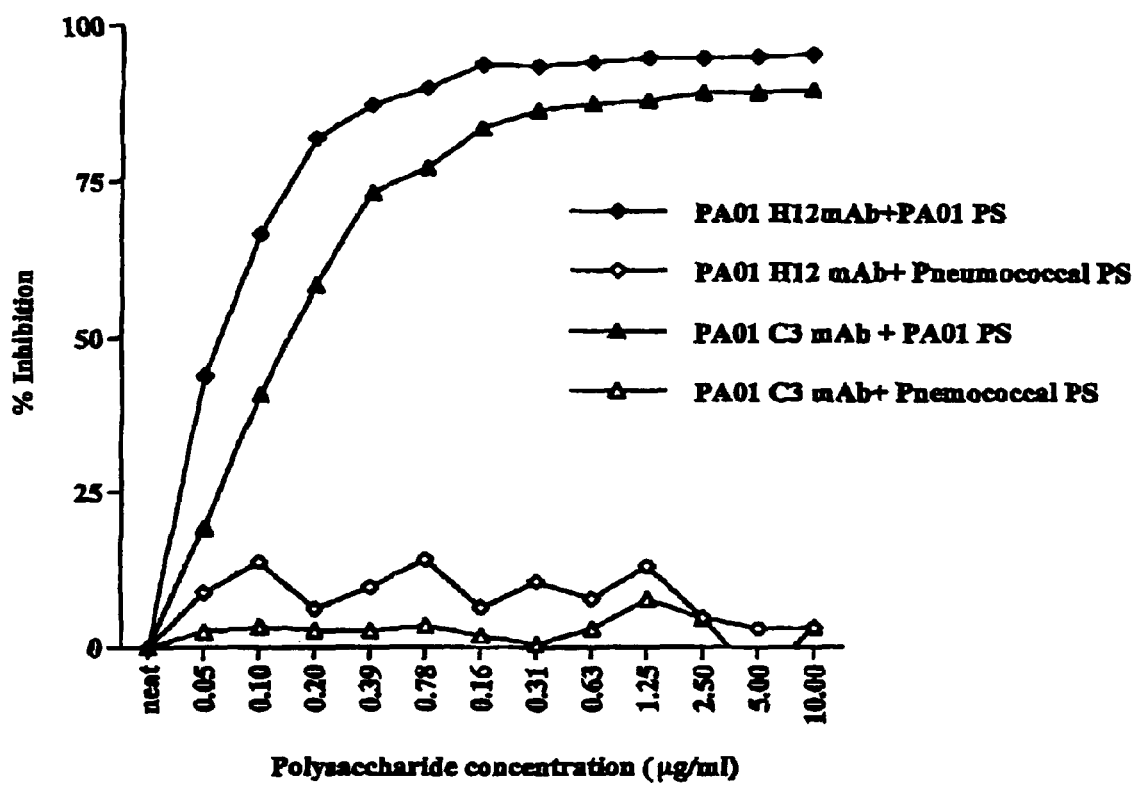
FIG. 7 depicts binding inhibition assays that show the H12 and C3 human monoclonal antibodies binding with specificity to the *Pseudomonas aeruginosa* LPS. Soluble *Pseudomonas aeruginosa* PA01 LPS, but not soluble Pneumococcal 6B control polysaccharide, was able to inhibit binding to solid phase *Pseudomonas aeruginosa* PA01 LPS.

In accordance with the present invention, there are provided fully human isolated antibodies or antigen-binding portions thereof that specifically binds to *Pseudomonas aeruginosa* LPS. In a preferred embodiment, the fully human antibodies are monoclonal. Other preferred embodiments include nucleotide sequences encoding and amino acid sequences comprising the antibodies' heavy and light chains, and in particular sequences corresponding to a contiguous heavy and light chain sequences from CDR1 through CDR3. Further provided are antibodies having similar binding properties and antibodies (or other antagonists) having similar functionality as antibodies disclosed herein. Hybridomas expressing such immunoglobulin molecules and monoclonal antibodies are also provided.

The terms herein generally have their usual meaning as understood by those of ordinary skill in the art. The following terms are intended to have the following general meanings as they are used herein:

"B lymphocytic cells or progeny thereof" refer to any cell descending from, or destined for, the B lymphocytic lineage. Examples include, but are not limited to, all B lymphocytes in the B cell developmental pathway starting from the earliest B lymphocyte stem cells through memory B cells, plasma cells, and any hybridomas created in vitro.

"Bispecific antibodies" are single antibodies that have affinities for two separate antigens. For example, a bispecific antibody might recognize *Pseudomonas aeruginosa* LPS using one combination of heavy and light chains and might recognize a leukocyte cell surface marker using a second combination of heavy and light chains attached to the first combination. See McCormick et al. *J. Immunol.* 158:3474-3482 (1997).

"Chimeric antibodies" are antibodies that have been altered from their original form to comprise amino acid sequences from another protein. Chimeric antibodies retain at least a portion of the original antibody amino acid sequence, typically the portion comprising the antigen binding region ($F_{ab}$). Examples of chimeric antibodies include, but are not limited to, bispecific antibodies and fusions with other non-immunoglobulin protein sequences.

"Cytokines" refer generally to signaling molecules of the immune system. Cytokines include, but are not limited to, Interleukins (IL), transforming growth factors (TGF), tumor necrosis factors (TNF), lymphotoxins (LT), interferons, granulocyte-macrophage colony stimulating factors (GM-CSF), macrophage CSF, Granulocyte CSF, and migration inhibition factors.

"Derivatize" refers to the process of attaching a non-immunoglobulin agent to the immunoglobulin molecules. Examples of derivatizing agents include, but are not limited to, toxins, complement, antibiotics, peptides, polysaccharides, lipids, organic polymers, radiolabels, and inorganic compounds.

"Expression control sequences" refer to sequences that allow for the inducible or constitutive expression of gene sequences under specific conditions or in specific cells. Examples of cellular processes that expression control sequence regulate include, but are not limited to, gene transcription, protein translation, messenger RNA splicing, immunoglobulin isotype switching, protein glycosylation, protein cleavage, protein secretion, intracellular protein localization and extracellular protein homing.

"Fusion Proteins" refer to chimeric proteins comprising amino acid sequences of two or more different proteins. Typically, fusion proteins result from in vitro recombinatory techniques well known in the art. However, fusion proteins may result from in vivo crossover or other recombinatory events.

"Human immunoglobulin molecules" refer to immunoglobulin proteins that are encoded by human immunoglobulin gene sequences. The immunoglobulin gene sequences may be expressed in any non-human animal.

"Human monoclonal antibodies" refer to antibodies that are members of a population of human antibodies with identical specificities. The population of human antibodies may be produced in a hybridoma or other immortalized cell line as well as in recombinant cell lines expressing the exogenous human antibody gene sequences.

"Immunocompromised patients" refer to patients whose immune responses to foreign antigens or agents is impaired either by disease (e.g. AIDS), by invasive surgery, or by drug therapies in connection with treatments for other conditions (e.g. organ transplant patients).

"Label" refers to any molecule that attaches to the claimed immunoglobulin a functional characteristic not normally associated with that immunoglobulin. Labels can be attached via chemical modification of the immunoglobulin, recognition of the label by one of the two $F_{ab}$ regions of a bispecific immunoglobulin, affinity for a third agent (e.g. the avidin/biogen interaction), radiolabeling, or as a fusion protein expressed recombinantly. Labels can function as molecular or radioactive tags for clinical or research purposes or as agents for combating *Pseudomonas aeruginosa* infection (e.g. toxins or complement proteins). Other examples of labels can include enzymes, fluorescent molecules, magnetic labels, epitope tags (e.g. *H. influenza* hemaglutinin), antibiotics, complement proteins, and cytokines.

"Respiratory patients" refer to any patient that is either being treated for a disease of the respiratory system or is receiving respiratory care, e.g. intubation or ventilation, in connection with some other medical treatment.

"Surgical patients" refer to any patient that is subject to an invasive surgical procedure, typically involving puncturing or incising the dermis.

"Toxins" refer to protein or non-protein compounds that can be attached to antibodies for the purpose of killing the cells to which the antibodies have attached. Examples of toxins include, but are not limited to, complement, antibiotics, peptides, polysaccharides, lipids, organic polymers, radiolabels, and inorganic compounds.

"Vectors" refer to DNA molecules that allow DNA sequences of interest to be cloned, propagated, recombined, mutated, or expressed outside of their native cells. Often vectors have expression control sequences that allow for the inducible or constitutive expression of gene sequences under specific conditions or in specific cells. Examples of vectors include, but are not limited to, plasmids, yeast artificial chromosomes (YACs), viruses, bacteriophages, and phagemids.

"XenoMouse™" refers to mice bearing homologously targeted endogenous immunoglobulin loci, rendering them incapable of expressing endogenous murine immunoglobulin, but bearing substantial portions of human immunoglobulin loci. Mice of the XenoMouse™ line are capable of somatic rearrangement of the human immunoglobulin genes, hypermutation of the human variable genes, and immunoglobulin isotype switching. Therefore, the mice of the XenoMouse™ line are capable of mounting effective humoral responses to antigenic challenge utilizing the human immunoglobulin gene sequences. The resulting antibodies are fully human and can be isolated from the animals themselves, from cultured cells extracted from the animals, and from hybridomas created from XenoMouse™ B lymphocytic lines or progeny thereof. Moreover, the rearranged human gene sequences encoding immunoglobulins raised against specific antigenic challenges can be isolated by recombinant means well known in the art.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79:315-321 (1990), Kostelny et al. *J. Immunol.* 148:1547-1553 (1992). In addition, bispecific antibodies may be formed as "diabodies" (Holliger et al. "'Diabodies': small bivalent and bispecific antibody fragments" *PNAS USA* 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int J Cancer Suppl* 7:51-52 (1992)). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies from Non-Human Animals

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one can develop humanized antibodies or generate fully human antibodies through the introduction of human antibody function into a rodent so that the rodent would produce fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, cancer and bacterial infections, which potentially require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J. Exp. Med.* 188:483-495 (1998), and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146-156 (1997) and Green and Jakobovits *J. Exp. Med.* 188:483-495 (1998). See also European Patent No. EP 0 463 151 B1, grant published Jun. 12, 1996, International Patent Application No. WO 94/02602, published Feb. 3, 1994, International Patent Application No. WO 96/34096, published Oct. 31, 1996, and WO 98/24893, published Jun. 11, 1998. The disclosures of each of the above-cited patents, applications, and references are hereby incorporated by reference in their entirety.

Antibodies in accordance with the present invention are preferably prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving the same are disclosed in the patents, applications, and references disclosed herein.

Through use of such technology, fully human monoclonal antibodies, or the antigen binding portions thereof, to *Pseudomonas aeruginosa* LPS were produced. Essentially, we immunized XenoMouse™ lines of mice with heat killed *Pseudomonas aeruginosa*, recovered spleen and lymph node cells (such as B-cells) from the mice that express *Pseudomonas aeruginosa* LPS antibodies, fused such recovered cells with nonsecreting myeloma cells to prepare immortal hybridoma cell lines, and screened hybridoma cell lines to identify those that produce antibodies specific to the antigen of interest.

As will be appreciated, antibodies in accordance with the present invention can be expressed in cell lines other than hybridoma cell lines. Sequences encoding particular antibodies can be used for transformation of a suitable host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, NS/O, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive *Pseudomonas aeruginosa* LPS binding properties.

Further, expression of antibodies of the invention (or other moieties therefrom) from production cell lines can be enhanced using a number of known techniques. For example, enhanced expression can be realized by the coamplification expression system utilizing dihydrofolate reductase (DHFR) or the glutamine synthetase gene expression system (the GS system). See, e.g. Kaufman and Sharp *J. Mol. Biol.* 159:601-621 (1982); European Patent Nos. 0 216 846, 0 256 055, and 0 323 997; and European Patent Application No. 89303964.4.

Antibodies of the invention can also be produced through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

The invention contemplates an isolated human antibody or antigen-binding portion thereof that was expressed in a non-human animal and specifically binds to *Pseudomonas aeruginosa* LPS. In a preferred embodiment, the isolated human antibody or antigen-binding portion thereof is a monoclonal antibody.

The invention further contemplates the isolated human antibody or antigen-binding portion thereof that is opsonic for *Pseudomonas aeruginosa* cells. In a preferred embodiment, the isolated human antibody or antigen-binding portion thereof facilitates phagocytosis of the *Pseudomonas aeruginosa* cells.

The invention also contemplates that the isolated human antibody or antigen-binding portion thereof enhances the immune response to *Pseudomonas aeruginosa*. In a preferred embodiment, the isolated human antibody or antigen-binding portion thereof facilitates the killing of *Pseudomonas aeruginosa* cells. In a more preferred embodiment, the isolated human antibody or antigen-binding portion thereof facilitates the killing of *Pseudomonas aeruginosa* cells by delivering an agent that is lethal to the *Pseudomonas aeruginosa* cells.

The invention contemplates an isolated human antibody or antigen-binding portion thereof that specifically binds to *Pseudomonas aeruginosa* LPS, wherein the antibody or antigen-binding portion thereof inhibits *Pseudomonas aeruginosa* infection.

The invention also contemplates an isolated human antibody or antigen-binding portion thereof that specifically binds to *Pseudomonas aeruginosa* LPS, wherein the antibody or antigen-binding portion thereof binds to *Pseudomonas aeruginosa* LPS with a dissociation constant ($K_d$) of $5\times10^{-7}$ M or less, preferably $5\times10^{-7}$ M to $1\times10^{-7}$ M. In a more preferred embodiment, the antibody or antigen-binding portion thereof binds to *Pseudomonas aeruginosa* LPS with a $K_d$ of $1\times10^{-7}$ M to $5\times10^{-8}$ M. In a more preferred embodiment, the antibody or antigen-binding portion thereof binds to *Pseudomonas aeruginosa* LPS with a $K_d$ of $5\times10^{-8}$ M to $1\times10^{-8}$ M.

The invention contemplates an isolated human antibody or antigen-binding portion thereof that specifically binds to *Pseudomonas aeruginosa* LPS and has a half-life in vivo of one hour or more. In a preferred embodiment, the antibody or antigen-binding portion thereof has a half-life in vivo of between one and thirty days. In a more preferred embodiment, the antibody or antigen-binding portion thereof has a half-life in vivo of between sixteen and thirty days. In another more preferred embodiment, the antibody or antigen-binding portion thereof has a half-life in vivo of between one hour and fifteen days.

The isolated human antibody or antigen-binding portion thereof that specifically binds to *Pseudomonas aeruginosa* LPS of the invention may be immunoglobulin G (IgG), IgM, IgE, IgA and IgD. In a preferred embodiment, the IgG may be an IgG1, IgG2, IgG3 or IgG4 subtype.

The invention contemplates an isolated human antibody or antigen-binding portion thereof that specifically binds to *Pseudomonas aeruginosa* LPS and is labeled. In a preferred embodiment, the label is a radiolabel, an enzyme label, a fluorescent label, a toxin, a magnetic agent, a second antibody, an affinity label, an epitope tag, an antibiotic, a complement protein or a cytokine.

The invention contemplates an isolated human antibody or antigen-binding portion thereof that specifically binds to *Pseudomonas aeruginosa* LPS and comprises a kappa light chain and framework sequences thereof. In a preferred embodiment, the framework sequences of the kappa light chain are encoded by a human V 2/A2 gene. In a preferred embodiment, the kappa light chain comprises between seven and fifteen changes from a kappa light chain encoded by a germline V 2/A2 gene. In a more preferred embodiment, the kappa light chain comprises no more than six amino acid changes from a kappa light chain encoded by a germline V 2/A2 gene. In a more preferred embodiment, the kappa light chain comprises no more than three amino acid changes from a kappa light chain encoded by a germline V 2/A2 gene.

The invention contemplates an isolated human antibody or antigen-binding portion thereof that specifically binds to *Pseudomonas aeruginosa* LPS and comprises a kappa light chain having the amino acid sequence of SEQ ID NO: 4. The invention further contemplates an isolated human antibody or antigen-binding portion thereof that specifically binds to *Pseudomonas aeruginosa* LPS and comprises a kappa light chain that is encoded by the nucleic acid sequence of SEQ ID NO: 3. The invention also contemplates an isolated human antibody or antigen-binding portion thereof that specifically binds to *Pseudomonas aeruginosa* LPS and comprises a lambda light chain.

The invention contemplates an isolated human antibody or antigen-binding portion thereof that specifically binds to *Pseudomonas aeruginosa* LPS, comprising a heavy chain composed of variable (V), diversity (D), and Joining (J) regions and composed of framework sequences thereof. In a preferred embodiment, the variable region of the heavy chain is encoded by a human $V_H3$/V3-33 gene. In another preferred embodiment, the diversity region of the heavy chain is encoded by a human D2-8 gene. In another preferred embodiment, the joining region of the heavy chain is encoded by a human $J_H4b$ gene. In a more preferred embodiment, the variable region comprises between seven and fifteen amino acid changes from a variable region encoded by a germline $V_H3$/V3-33 gene. In a more preferred embodiment, the heavy chain comprises no more than six amino acid changes from a variable region encoded by a germline $V_H3$/V3-33 gene. In a more preferred embodiment, the heavy chain comprises no more than three amino acid changes from a variable region encoded by a germline $V_H3$/V3-33 gene.

The invention contemplates an isolated human antibody or antigen-binding portion thereof that specifically binds to *Pseudomonas aeruginosa* LPS and comprises a heavy chain having the amino acid sequence of SEQ ID NO: 2.

The invention contemplates an isolated human antibody or antigen-binding portion thereof that specifically binds to *Pseudomonas aeruginosa* LPS and is encoded by the nucleic acid sequence of SEQ ID NO: 1.

The invention contemplates an isolated human antibody or antigen-binding portion thereof that specifically binds to *Pseudomonas aeruginosa* LPS and comprises an antigen binding domain chosen from the list consisting of an Fab fragment, an $F(ab')_2$ fragment and an $F_v$ fragment.

The invention contemplates an isolated human antibody or antigen-binding portion thereof that specifically binds to *Pseudomonas aeruginosa* LPS and the antibody is a single chain antibody.

The invention contemplates an isolated human antibody or antigen-binding portion thereof that specifically binds to *Pseudomonas aeruginosa* LPS and the antibody is a chimeric antibody. In a preferred embodiment, the chimeric antibody comprises framework regions and CDR regions from different human antibodies. In a more preferred embodiment, the chimeric antibody is bispecific. In a more preferred embodiment, the chimeric antibody is bispecific for *Pseudomonas aeruginosa* LPS and a label selected from the list consisting of a radiolabeled molecule, an enzymatic label, a fluorescent label, a toxin, a magnetic agent, a second antibody, an affinity label, an epitope tag, an antibiotic, a complement protein and a cytokine.

The invention contemplates an isolated human antibody or antigen-binding portion thereof that specifically binds to *Pseudomonas aeruginosa* LPS and the antibody or portion thereof is derivatized. In a preferred embodiment, the antibody or portion thereof is derivatized with polyethylene glycol, at least one methyl or ethyl group or at least one carbohydrate moiety.

The invention contemplates a pharmaceutical composition comprising the an isolated human antibody or antigen-binding portion thereof that specifically binds to *Pseudomonas aeruginosa* LPS and a pharmaceutically acceptable carrier. The invention further contemplates a kit comprising the antibody or antigen-binding portion thereof, a pharmaceutically acceptable carrier therefor, and a container. In a preferred embodiment, the kit further comprising instructions for use.

The invention contemplates a method for treating or preventing *Pseudomonas aeruginosa* infection, comprising the step of administering a pharmaceutical composition to a patient at risk of being infected with, or currently infected with, *Pseudomonas aeruginosa*.

In a preferred embodiment, the human antibody is a monoclonal antibody. In another preferred embodiment, the pharmaceutical composition is administered via an injection, trasmucosal, oral, inhalation, ocular, rectal, long acting implantation, liposomes, emulsion, cream, topical or sustained release means. In another preferred embodiment, the antibody is a fusion with a second protein. In a more preferred embodiment the second protein is chosen from the list consisting of a toxic peptide moiety, a complement protein, a radiolabeled protein, a cytokine or an antibiotic protein. In another preferred embodiment, the antibody is labeled with a radiolabel, a toxin, a complement protein, a cytokine or an antibiotic. In another preferred embodiment, the patient is a burn patient, a surgical patient, a prosthesis recipient, a respiratory patient, a cancer patient, a cystic fibrosis patient or an immunocompromised patient. In another preferred embodiment, the pharmaceutical composition further comprises toxins, complement proteins, radiolabeled proteins, cytokines, antibiotics, or any combination thereof.

The invention contemplates an isolated cell line that produces a human antibody or antigen-binding portion thereof that specifically binds to *Pseudomonas aeruginosa* LPS. In a preferred embodiment, the cell line is a hybridoma.

The invention contemplates a method of producing an isolated human antibody or antigen-binding portion thereof that specifically binds to *Pseudomonas aeruginosa* LPS, comprising:
  a) culturing a non-human cell capable of producing the antibody under conditions in which the antibody is produced;
  b) isolating the antibody from the cell culture.

In a preferred embodiment, the method of producing an isolated human antibody or antigen-binding portion thereof that specifically binds to *Pseudomonas aeruginosa* LPS utilizes a hybridoma. In another preferred embodiment, the method utilizes a cell that is transformed with isolated nucleic acid molecules encoding the human antibody or antigen-binding portion thereof and the cell is chosen from the list consisting of a bacterial cell, a yeast cell, an insect cell, an amphibian cell and a mammalian cell. In a more preferred embodiment, the mammalian cell is selected from the list consisting of a human cell, a mouse cell, a rat cell, a dog cell, a monkey cell, a goat cell, a pig cell, a bovine cell and a hamster cell. In a more preferred embodiment, the mammalian cell is selected from the list consisting of a HeLa cell, a NIH 3T3 cell, a CHO cell, a BHK cell, a VERO cell, a CV-1 cell, a NS/0 cell and a COS cell.

The invention contemplates a method for making an isolated human antibody or antigen-binding portion thereof that specifically binds to *Pseudomonas aeruginosa* LPS, comprising:
  a) immunizing a non-human animal having incorporated a human immunoglobulin locus therein with a *Pseudomonas aeruginosa* antigenic composition;
  b) allowing the non-human animal to mount a humoral response to the antigenic composition; and
  c) isolating the human antibody from the non-human animal.

The invention contemplates a nucleic acid molecule isolated from a non-human animal that encodes a human antibody heavy chain or the antigen-binding portion thereof that specifically binds to *Pseudomonas aeruginosa* LPS. In a preferred embodiment, the nucleic acid molecule is isolated from a hybridoma that produces the human antibody.

The invention contemplates an isolated nucleic acid molecule, or a fragment thereof, encoding a human antibody heavy chain or antigen-binding portion thereof that specifically binds to *Pseudomonas aeruginosa* LPS having the nucleotide sequence of SEQ ID: 1. In a preferred embodiment, the isolated nucleic acid molecule comprises the sequence encoding between one to three of the CDR regions of the human antibody.

The invention contemplates a vector comprising a nucleic acid molecule, or fragment thereof, encoding a human antibody heavy chain or antigen-binding portion thereof that specifically binds to *Pseudomonas aeruginosa*. In a preferred embodiment, the vector further comprises expression control sequences operably linked to the nucleic acid.

The invention contemplates a nucleic acid molecule isolated from a non-human animal that encodes a human antibody light chain or the antigen-binding portion thereof that specifically binds to *Pseudomonas aeruginosa* LPS. In a preferred embodiment, the nucleic acid molecule is isolated from a hybridoma that produces the human antibody.

The invention contemplates an isolated nucleic acid molecule, or a fragment thereof, encoding a human antibody light chain or antigen-binding portion thereof that specifically binds to *Pseudomonas aeruginosa* LPS having the nucleotide sequence of SEQ ID: 3. In a preferred embodiment, the isolated nucleic acid molecule comprises the sequence encoding between one to three of the CDR regions of the human antibody.

The invention contemplates a vector comprising a nucleic acid molecule, or fragment thereof, encoding a human antibody light chain or antigen-binding portion thereof that specifically binds to *Pseudomonas aeruginosa*. In a preferred embodiment, the vector further comprises an expression control sequence operably linked to the nucleic acid.

The invention contemplates an isolated host cell comprising
  a) a nucleic acid molecule that was isolated from a non-human animal and encodes a light chain or the antigen-binding portion thereof of a human antibody that specifically binds to *Pseudomonas aeruginosa* LPS; or
  b) a vector comprising the nucleic acid molecule.

The invention contemplates an isolated host cell comprising:
  a) a nucleic acid molecule that was isolated from a non-human animal and encodes a heavy chain or the antigen-binding portion thereof of a human antibody that specifically binds to *Pseudomonas aeruginosa* LPS; or
  b) a vector comprising the nucleic acid molecule.

The invention contemplates an isolated host cell comprising:
  a) a nucleic acid molecule that was isolated from a non-human animal and encodes a heavy chain or the antigen-binding portion thereof and an isolated nucleic acid molecule that encodes a light chain or the antigen-binding portion thereof of a human antibody that specifically binds to *Pseudomonas aeruginosa* LPS; or
  b) a vector or vectors comprising the nucleic acid molecules.

In a preferred embodiment, the isolated host cells described above are chosen from the list consisting of hybridoma cells, bacterial cells, yeast cells, insect cells, amphibian cells and mammalian cells. In a more preferred embodiment, the mammalian cells are selected from the list consisting of human cells, mouse cells, rat cells, dog cells, monkey cells, goat cells, pig cells, bovine cells and hamster cells. In a more preferred embodiment, the mammalian cells are selected from the list consisting of HeLa cells, NIH 3T3 cells, CHO cells, BHK cells, VERO cells, CV-1 cells, NS/0 cells and COS cells.

The invention contemplates a method of recombinantly producing the heavy chain or the antigen-binding portion thereof, the light chain or the antigen-binding portion thereof, or both the light chain and heavy chain or antigen-binding portions thereof, of a human antibody that was identified from a non-human animal and specifically binds to *Pseudomonas aeruginosa* LPS, comprising the step of cultivating the host cells described above under conditions in which the nucleic acid molecules are expressed.

The invention contemplates an isolated human antibody heavy chain or antigen-binding portion thereof that specifically binds to *Pseudomonas aeruginosa* LPS, encoded by any of the nucleic acid molecules encoding the heavy chain described above, or isolated from any of the host cells described above. In a preferred embodiment, the isolated human antibody heavy chain or antigen-binding portion thereof comprises between one to ten amino acid substitutions that increase the serum half-life of the antibody.

The invention contemplates an isolated human antibody light chain or antigen-binding portion thereof that specifically binds to *Pseudomonas aeruginosa* LPS, encoded by any of the nucleic acid molecules encoding the heavy chain described above, or isolated from any of the host cells described above. In a preferred embodiment, the isolated human antibody light chain or antigen-binding portion thereof comprises between one to ten amino acid substitutions that increase the serum half-life of the antibody.

The invention contemplates a non-human transgenic animal comprising any of the nucleic acid molecules described above. In a preferred embodiment, the non-human transgenic animal expresses the nucleic acid molecule or molecules. In a more preferred embodiment, the non-human transgenic animal comprises an isolated nucleic acid molecule that encodes a heavy chain or the antigen-binding portion thereof and an isolated nucleic acid molecule that encodes a light chain or the antigen-binding portion thereof of a human antibody that specifically binds to *Pseudomonas aeruginosa* LPS, and the non-human animal expresses both nucleic acid molecules. In a more preferred embodiment, the non-human animal is selected from the list consisting of a mouse, a rat, a hamster, a cow, a sheep, a primate, a horse and a pig. In a more preferred embodiment, a human antibody resulting from expression of the isolated nucleic acid molecules or portions thereof is expressed on the surface of cells derived from the animal's B lymphocytic cells or progeny thereof. In another preferred embodiment, the human antibody resulting from expression of the isolated nucleic acid molecules or a portion thereof is secreted into the lymph, blood, milk, saliva, or ascites of the animal.

The invention contemplates a fusion protein comprising the an isolated human antibody or antigen-binding portion thereof that specifically binds to *Pseudomonas aeruginosa* LPS and a second polypeptide sequence. In a preferred embodiment, the second polypeptide sequence is chosen from the list consisting of an epitope tag, an affinity tag, a toxic polypeptide, an antibiotic, an enzyme, a second antibody sequence, a complement protein, and a cytokine.

The invention contemplates an isolated human antibody or antigen-binding portion thereof that specifically binds to *Pseudomonas aeruginosa* LPS, wherein the heavy chain isotype of the antibody is mu, gamma, delta, epsilon or alpha.

The invention contemplates an isolated human antibody or antigen-binding portion thereof that specifically binds to *Pseudomonas aeruginosa* LPS, wherein the antibody or antigen-binding portion thereof is produced by a process comprising the steps of:

a) immunizing a non-human animal comprising a human immunoglobulin locus with an antigen selected from the group consisting of an isolated *Pseudomonas aeruginosa* LPS preparation, a virile *Pseudomonas aeruginosa* cell preparation, an attenuated *Pseudomonas aeruginosa* cell preparation, and a killed *Pseudomonas aeruginosa* cell preparation;

b) allowing the non-human animal to mount an immune response to the antigen; and c) isolating the antibody from the non-human animal.

The invention contemplates an isolated human antibody or antigen-binding portion thereof that specifically binds to *Pseudomonas aeruginosa* LPS wherein the *Pseudomonas aeruginosa* LPS is derived from a *Pseudomonas aeruginosa* strain chosen from the list consisting of 06ad, 011, Habs16, 170003 and PA01 Halloway.

The invention contemplates an isolated human antibody or antigen-binding portion thereof isolated from an animal or cell that was free of contaminating human biomaterials. In a preferred embodiment, the biomaterials are viruses, enzymes, hormones, cytokines, receptors, receptor ligands, immunoglobulins, complement, nuclear proteins, and cytoplasmic signaling proteins. In a more preferred embodiment, the viruses are Epstein-Barr virus or retroviruses.

Pharmaceutical compositions may be manufactured by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For ocular administration, suspensions in an appropriate saline solution are used as is well known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually with a greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The isolated human antibody or antigen-binding portion thereof that specifically binds to *Pseudomonas aeruginosa* LPS of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

A component of the kits of the present invention comprise instructions for utilizing the compositions of the present invention for prevention or treatment of *Pseudomonas aeruginosa* infections. Applicant has, for the first time, disclosed herein a method of preventing or treating *Pseudomonas aeruginosa* infections with an isolated human antibody or antigen-binding portion thereof that specifically binds to *Pseudomonas aeruginosa* LPS. The printed instructions on the kit enable one of skill in the art to utilize the kit for practicing the methods of the present invention.

Example 1

Generation of Mice and Hybridomas that Produce Fully Human Antibodies to *Pseudomonas aeruginosa* LPS A. *Pseudomonas aeruginosa* Serotype 06ad

*Pseudomonas aeruginosa* serotype 06ad was used for mouse immunizations, mouse protection assays and opsonic assays. Bacteria for mouse challenge assays were fresh plated onto pseudosel agar (BBL, Becton Dickinson, Sparks, Md.), then were incubated at 37° C., and one cfu was inoculated into LB broth and was incubated at 37° C. in a shaking water bath to a concentration of $5 \times 10^8$ cfu/ml. Bacteria were centrifuged at 10,000 rpm for 5 minutes, resuspended and washed in chilled phosphate buffered saline (PBS). Bacteria for immunizations were grown as above and heat-killed at 60° C. for one hour and stored at 4° C. until use. Labeled bacteria used in the flow cytometry opsonic assay were grown and heat-killed as above. However, these bacteria were resuspended in Alkaline Conjugation Buffer (ACB: a 1:3 solution of 0.5M $Na_2CO_3$ and 0.5M $NaHCO_3$, pH 9.5) to give a concentration of $10^9$/ml. An equal volume of ACB with 0.06% Fluorescein Isothiocyanate Isomer I (FITC, Amresco, Solon, Ohio) was added and incubated for 20 hours at room temperature with gentle shaking. Bacteria were washed in veronal buffered saline and then were resuspended in PBS at $10^9$/ml, and stored at $-80°$ C.

The high molecular weight polysaccharide portion of the LPS O-specific side chains from *Pseudomonas aeruginosa* strains 06ad, 011, Habs16, 170003, and PA01 Halloway LPS (high MW PS) were made as described, and were lyophilized for storage. See Hatano et al. *Infect. Immun.* 62:3608-3616 (1994). These high MW PS were used to coat 96-well plates for enzyme-linked immunosorbent assays (ELISA) as described below. The 06ad high MW PS was also used in blocking and avidity assays described below.

Mice that were transgenic for human heavy and light Ig were bred and maintained by Abgenix Inc., Fremont, Calif. The strain of Xenomouse™ used was Xma2a-3, which is an Ig-inactivated mouse reconstituted with a YAC containing cointegrated human heavy and light chain transgenes. Mice were housed in micro-isolator cages in a pathogen-free facility after shipping, and food and water were autoclaved prior to use. Mice were immunized with $10^7$ heat-killed *Pseudomonas aeruginosa* 06ad PA twice per week intraperitoneally (ip) ($10^7$ bacteria in PBS) and/or in the foot pad ($10^7$ bacteria and RIBI adjuvant, Sigma, St. Louis, Mo.), and their sera screened for anti-*Pseudomonas aeruginosa* 06ad LPS antibodies by ELISA described below.

Hybridomas were generated by fusing spleen and/or lymph node cells from immunized, seropositive Xenomouse™ animals with the nonsecreting sp2/0 myeloma cell line, as described previously. See Mendez et al. *Nat. Gen.* 15:146-156 (1997); Schreiber et al. *J. Immunol.* 146:188-193 (1991). Supernatants from hybridomas were screened for production of human anti-*Pseudomonas aeruginosa* 06ad LPS using the ELISA procedure described below, and hybridomas found to be secreting IgG anti-LPS antibodies were then cloned three times by limiting dilution. One IgG2-secreting clone (S20) was chosen based on initial measurements of strength of binding to solid phase *Pseudomonas aeruginosa* 06ad PS.

B. *Pseudomonas aeruginosa* serotypes PA01 and 170003

*Pseudomonas aeruginosa* serotypes PA01 and 170003 were used for mouse immunizations. Bacteria were fresh plated onto pseudosel agar (BBL, Becton Dickinson, Sparks, Md.), then were incubated at 37° C., and one cfu was inoculated into LB broth and was incubated at 37° C. in a shaking water bath to a concentration of $5 \times 10^8$ cfu/ml. Bacteria were centrifuged at 10,000 rpm for 5 minutes, resuspended and washed in chilled phosphate buffered saline (PBS). Bacteria for immunizations were grown as above and heat-killed at 60° C. for one hour and stored at 4° C. until use.

The high molecular weight polysaccharide portion of the LPS O-specific side chains from *Pseudomonas aeruginosa* strains 06ad, 011, Habs16, 170003, and PA01 Halloway LPS (high MW PS) were made as described, and were lyophilized for storage. See Hatano et al. *Infect. Immun.* 62:3608-3616 (1994). These high MW PS were used to coat 96-well plates for enzyme-linked immunosorbent assays (ELISA) as described below. The PA01 and 170003 high MW PS also were used in blocking assays described below.

Mice that were transgenic for human heavy and light Ig were bred and maintained by Abgenix Inc., Fremont, Calif. The strain of Xenomouse™ used was Xma2a-3, which is an Ig-inactivated mouse reconstituted with a YAC containing cointegrated human heavy and light chain transgenes. Mice were housed in micro-isolator cages in a pathogen-free facility after shipping, and food and water were autoclaved prior to use. Mice were immunized with $10^7$ heat-killed *Pseudomonas aeruginosa* PA01 or 170003 twice per week intraperitoneally (ip) ($10^7$ bacteria in PBS) and/or in the foot pad ($10^7$ bacteria and RIBI adjuvant, Sigma, St. Louis, Mo.), and their sera screened for anti-*Pseudomonas aeruginosa* PA01 or 170003 LPS antibodies, respectively, by ELISA described below.

Hybridomas were generated by fusing spleen and/or lymph node cells from immunized, seropositive Xenomouse™ animals with the nonsecreting sp2/0 myeloma cell line, as described previously. See Mendez et al. *Nat. Gen.* 15:146-156 (1997); Schreiber et al. *J. Immunol.* 146:188-193 (1991). Supernatants from hybridomas were screened for production of human anti-*Pseudomonas aeruginosa* LPS using the ELISA procedure described below, and hybridomas found to be secreting anti-LPS antibodies were then cloned three times by limiting dilution. Two IgM-secreting clones (H12 and C3) were chosen based on initial measurements of strength of binding to solid phase *Pseudomonas aeruginosa* PA01 PS. These were derived from fusion of splenic cells as described above. One IgM-secreting clone (LN1H10) derived from fusion of lymph node cells was chosen based on initial measurements of strength of binding to solid phase *Pseudomonas aeruginosa* 170003 PS.

Example 2

Characterization and Usage of Variable Region Genes From Transgenic Mouse-Derived Anti-LPS Antibody Dideoxy DNA sequencing was performed as previously described to determine the sequence of the variable region of the human monoclonal antibodies (30, 33). Total RNA was isolated from hybridoma cells from nine different clones using TRIZOL reagent (Gibco BRL) and converted into random primed cDNA for use as a template in PCR. Human heavy chain and light chain variable regions were amplified using degenerate leader peptide primers and constant region primers provided in the Human Ig-Primer Set (Novagen, Madison, Wis.). The PCR products were analyzed on a Trisacetate-EDTA agarose gel. The positive PCR reactions were chloroform isoamyl alcohol (24:1) extracted and cloned into the EcoRI site of pT7Blue (Novagen). The clones were sequenced based on the dideoxy method with Sequenase V2.0 DNA sequencing kit (USB, Cleveland, Ohio). Gene usage analysis was performed using the Vbase database (Tomlinson et al., MRC Centre for Protein Engineering, Cambridge, UK:

Variable region genes from hybridomas obtained from fusion of spleen cells from PA-immunized transgenic mice with the non-secreting SP2/0 cell line were cloned and sequenced in order to determine variable region gene usage (FIG. 1). The protective IgG2 anti-LPS monoclonal antibody chosen for further study that was made in the human Ig transgenic mice, utilized genes from the $V_H3$ gene family, similar to the restricted $V_H$ gene usage found after immunization of humans with a variety of bacterial polysaccharides. Nine other Mab made from fusions with spleen cells from pseudomonas immunized transgenic mice yielded antibodies that also used the $V_H3$ gene family for the heavy chain gene elements as determined by DNA sequencing. More specifically, DNA sequence analysis showed that the $V_H3$/V3-33 and JH4 genes were used in the protective anti-LPS Mab. Similarly, light chain gene segments used were Vk2/A2 and Jk1, as is commonly used in humans after PS vaccine immunization. In summary, gene usage for anti-LPS antibodies after PA immunization in these transgenic mice appeared to be remarkably similar to that observed in humans after PS immunization.

Example 3

Detection of Anti-*Pseudomonas aeruginosa* LPS Antibodies

Enzyme-linked immunosorbent assay (ELISA) was used to detect antibodies to the *Pseudomonas aeruginosa* 06ad LPS in sera of immunized mice and in hybridoma supernatants as we have previously described (34). Briefly, 96-well microtiter polystyrene plates (NUNC, Denmark) were coated with 2 ug/ml of *Pseudomonas aeruginosa* 06ad high MW PS overnight at 4° C., washed, and blocked with 200 ul/well of 1% bovine serum albumin (BSA; Sigma-Aldrich, St. Louis, Mo.) in PBS and 0.05% Tween 20 (Amresco, Solon, Ohio). Plates were washed and incubated over night with serial dilutions of S20 or sera in 1% BSA in PBS. Plates were washed, and bound antibodies were detected by adding isotype specific alkaline phosphatase-conjugated mouse-anti-human polyclonal antibodies (Southern Biotechnology Associates, Birmingham, Ala.). Plates were developed with 100 ul/well of p-nitrophenyl phosphate (PNPP, Sigma-Aldrich) chromogenic substrate in DEA buffer. Optical densities were measured at 415 nm with a microplate reader (Biorad, Hercules, Calif.).

Blocking assays to determine the specificity of S20 were performed in an identical fashion as above except that soluble *Pseudomonas aeruginosa* 06ad high MW PS or control PS of different concentrations was added to the S20 prior to addition to PS-coated 96-well ELISA plates. Relative avidity of the Mab was calculated as described. See Chung et al. *Infect. Immun.* 63:4219-4223 (1995); Schreiber et al. *J. Infect. Dis* 167:221-226 (1993). Antibodies were added to the wells of a high MW PS-coated ELISA plate followed by serial dilutions of *Pseudomonas aeruginosa* 06ad high MW PS or equal volumes of PBS (negative control). The blocking assays to determine the binding specificity of the H12, C3 and LN1H10 monoclonal antibodies were conducted as described above, using soluble *Pseudomonas aeruginosa* PA01 or 170003 high MW PS. The concentration of PS required to inhibit 50% of the maximum absorbance was calculated ($I_{50}$) and the inverse of this value was used to represent relative avidity.

The S20 produced in the transgenic mouse was specific for the O-side chain of *P. aeruginosa* strain 06ad. Blocking assays revealed over 90% reduction in binding of S20 to solid phase *Pseudomonas aeruginosa* 06ad LPS high MW PS after preincubation of the Mab with the same PS, compared to less than 10% inhibition with the control PS (purified type 6B pneumococcal capsular PS; FIG. 2). S20, however, did not cross-react with LPS from other *P. aeruginosa* serotypes since no binding could be demonstrated to solid phase LPS O-side chain high MW PS from a variety of *pseudomonas* strains including 011, Habs 16, 170003, and PA01 Halloway (FIG. 3).

The concentration of high MW PS that inhibited 50% of the maximum absorbance of S20 binding to high MW PS was determined so that the inverse of this value ($1/I_{50}$) was used to calculate relative avidity of S20. This value was compared to a previously developed protective mouse monoclonal antibody directed to the same high MW PS and to previously published anti-polysaccharide values derived by using similar techniques (2, 33). We found that the relative avidity of the human Mab was higher than the mouse Mab (1.0 vs. 0.036).

Figure 8:
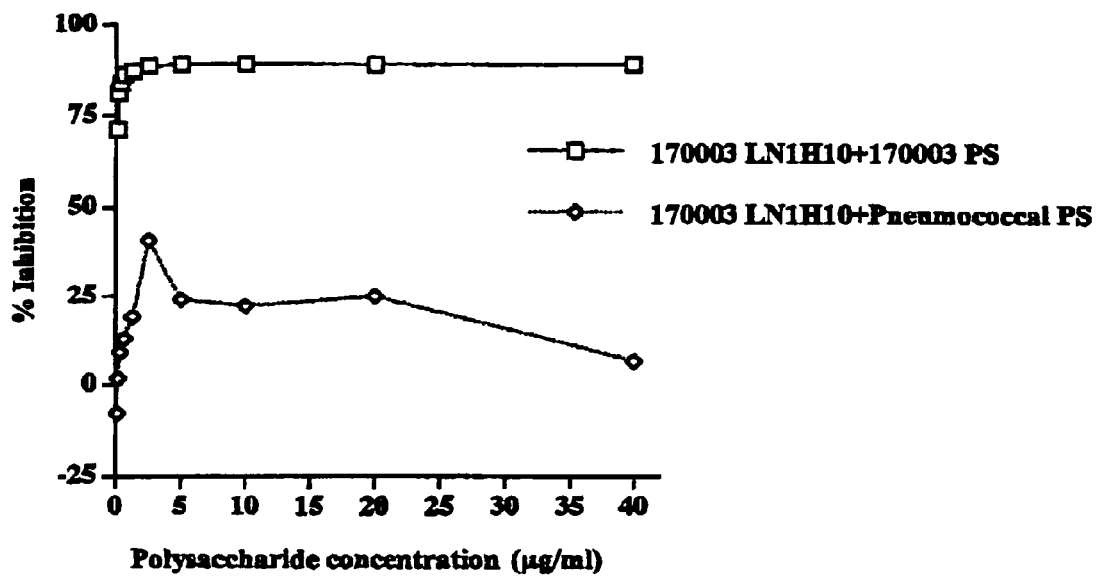
FIG. 8 depicts binding inhibition assays that show the LN1H10 human monoclonal antibody binding with specificity to the *Pseudomonas aeruginosa* LPS. Soluble *Pseudomonas aeruginosa* 170003 LPS, but not soluble Pneumococcal 6B control polysaccharide, was able to inhibit binding to solid phase *Pseudomonas aeruginosa* 170003 LPS.

Blocking assays with H12 and C3 revealed over 90% and 85% reduction, respectively, in binding to solid phase *Pseudomonas aeruginosa* PA01 LPS high MW PS after pre-incubation of the mAbs with the same PS, compared to less than 20% inhibition with the control PS (purified type 6B pneumococcal capsular PS; FIG. 7). Preincubation of LN1H10 with *Pseudomonas aeruginosa* 170003 LPS high MW PS reduced binding of the mAb to solid phase PS by 89% compared to less than 40% inhibition with the control PS (FIG. 8).

Example 4

Anti-*Pseudomonas aeruginosa* LPS Antibody Opsonization Promotes Complement-Dependent Phagocytosis The ability of the human monoclonal antibody to opsonize *P. aeruginosa* 06ad for uptake by human poly-morphonuclear leukocytes (PMN) was measured via flow cytometry as previously described. See Schreiber et al. *J. Infect. Dis* 167:221-226 (1993). *Pseudomonas aeruginosa* 06ad was grown, heat-killed and FITC labeled. Opsonization was carried out by incubating the labeled bacteria with S20 with or without 1% human serum from an agammaglobulinemic patient as the complement source. Bacteria were washed in PBS containing 6% dextran and 0.2% glucose, and then were resuspended in HBSS with 0.1% gelatin. Polymorphonuclear leukocytes (PMN) were isolated from peripheral human blood from healthy, adult volunteers. See Schreiber et al. *J. Infect. Dis* 167:221-226 (1993); Tosi et al. *J. Clin. Invest.* 86:300-308 (1990). MN were resuspended to achieve a concentration of $10^7$ cells/ml, and activated for 30 minutes with 10 ul of a $10^{-6}$ dilution per ml of cells of FMLP (Peninsula Laboratories, San Carlos, Calif.). PMNs were added to each opsonized bacteria sample, incubated at 37° C., and then were separated from free bacteria by differential centrifugation and resuspended in PBS. Single color flow cytometry analysis was performed on PMN utilizing a FACScan and CellQuest software (Becton Dickinson, MountainView, Calif.), and phagocytosis was expressed in relative units of mean fluorescence of 10,000 PMN for each sample. To demonstrate that the observed opsonophagocytosis was associated with bacterial killing, an alternative assay was used in which 10⁶ CFU of live *P. aeruginosa* 06ad was mixed with fresh human serum absorbed with the bacteria, S20 and 10⁶ fresh human PMN. Samples were obtained at the beginning and end of a 90 minute 37° incubation, bacteria were diluted and then plated for bacterial enumeration.

To show functional activity of the Anti-*Pseudomonas aeruginosa* 06ad LPS antibody, S20 was shown to be highly opsonic for uptake of labeled PA by fresh human PMN in a complement-dependent assay. In fact, the human Mab was almost two-fold more opsonic than a previously described protective mouse Mab (D8) against the same epitope (2.5 mg of human Mab yielded twice the mean fluorescence as 5 mg of mouse Mab; FIG. 4). Since the bacteria were heat killed prior to labeling with FITC it seemed possible that increased susceptibility to antibody and complement-mediated opsonization could have occurred due to damage to the bacterial surface. Thus, we also measured opsonization and phagocytosis of *Pseudomonas aeruginosa* 06ad in a killing assay in which 10⁶ CFU of live bacteria are opsonized with antibody and human complement and then colony counts determined after exposure to 10⁶ fresh PMN. The S20 Mab was also effective in this assay so that 5 mg/ml antibody resulted in 80% reduction in the PA cfu.

Example 5

Protection of Neutropenic Mice from Fatal *Pseudomonas aeruginosa* Sepsis

The protective efficacy of the human Mab against invasive infection with *Pseudomonas aeruginosa* was measured in the neutropenic mouse model, described previously. See Pier et al. *Infect. Immun.* 57:174-179 (1989); Schreiber et al. *J. Immunol.* 146:188-193 (1991). Female, six week-old BALB/c ByJ mice (Jackson Laboratories, Bar Harbor, Me.) were maintained in a pathogen-free, *pseudomonas*-free environment in which water, bedding, and food were autoclaved prior to use. Neutropenia was established by administering 3 mg of cyclophosphamide (Cytoxan®, Bristol-Myers Squibb, Princeton, N.J.) intra-peritoneally to each mouse on days 1, 3, and 5. On day 5, the cyclophosphamide was administered at time 0 hours, and 2 hours later 10 ug of S20 or PBS control was administered ip, followed by 10³ cfu of live *Pseudomonas aeruginosa* 06ad PA two hours later. Mice were observed daily thereafter and mortality was the outcome measured.

As illustrated in FIG. 5, infected mice treated with the PBS control began dying one day after *Pseudomonas aeruginosa* infection. After two days, 100% of the infected mice treated with PBS had died. In contrast, 100% of the mice treated with the S20 mAb showed protection and were alive two days after *Pseudomonas aeruginosa* infection, demonstrating the protective potential of S20 in preventing *Pseudomonas aeruginosa*-related fatalities in patients.

The embodiments listed above are for illustrative purposes only; the invention as contemplated is not limited to any of these particular embodiments and in fact may encompass a combination of one or more of the embodiments.

Biological Deposits

Hybridoma cell lines S20, H12, C3, and LN1H10 were deposited on Feb. 13, 2002, in accordance with the provisions of the Budapest Treaty at the American Type Culture Collection (ATCC), 10801 University Blvd., Manassas, Va. 20110-2209, USA. The S20, LN1H10, and C3 hybridoma cell lines were deposited on Feb. 13, 2002, and were assigned ATCC Accession Nos. HB PTA-4073, HB PTA-4074, and HB PTA-4075, respectively.

We claim:

1. The hybridoma cell line that produces the C3 monoclonal antibody, said hybridoma cell line having the American Type Culture Collection Accession Number PTA-4075.

2. A method of producing a monoclonal antibody reactive to *Pseudomonas aeruginosa*, the method comprising the culturing of the hybridoma cell line having the American Type Culture Collection Accession Number PTA-4074.

* * * * *

UNITED STATES PATENT AND TRADEMARK OFFICE
CERTIFICATE OF CORRECTION

PATENT NO.        : 9,089,557 B2
APPLICATION NO.   : 14/636753
DATED             : July 28, 2015
INVENTOR(S)       : John R. Schreiber and Kulwant Kamboj Kaur Page 1 of 1

It is certified that error appears in the above-identified patent and that said Letters Patent is hereby corrected as shown below:

In the Claims

Column 28, line 46 at line 4 of Claim 2, the text reading "PTA-4074", should be replaced with --PTA-4075--

Signed and Sealed this
Twenty-ninth Day of December, 2015

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 462
<212> TYPE: DNA
<213> ORGANISM: Homo sapiens
<220> FEATURE:
<221> NAME/KEY: CDS
<222> LOCATION: (1)..(462)

<400> SEQUENCE: 1 cag gtg cag ctg gtg gag tct ggg gga ggc gtg gtc cag cct ggg agg      48
Gln Val Gln Leu Val Glu Ser Gly Gly Gly Val Val Gln Pro Gly Arg
  1               5                  10                  15 tcc ctg aga ctc tcc tgt gca gcg tct gga ttc acc ttc agt agc tat      96
Ser Leu Arg Leu Ser Cys Ala Ala Ser Gly Phe Thr Phe Ser Ser Tyr
             20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
         35                  40                  45 gca gct ata tgg tat agt gga agt aat aaa tac tat gca gac tcc gtg     192
Ala Ala Ile Trp Tyr Ser Gly Ser Asn Lys Tyr Tyr Ala Asp Ser Val
     50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                 85                  90                  95
```

```
gcg aga gat ccc cac tat acc cgg ggt ttt gac tac tgg ggc aag gga     336
Ala Arg Asp Pro His Tyr Thr Arg Gly Phe Asp Tyr Trp Gly Lys Gly
            100                 105                 110 acc ctg gtc acc gtc tca gcc tcc acc aaa ggg ccc atc ggt ctt         384
Thr Leu Val Thr Val Ser Ser Ala Ser Thr Lys Gly Pro Ile Gly Leu
        115                 120                 125 ccc ctg gcg ccc tgc tcc agg agc acc tcc gag agc aca gcg gcc ctg     432
Pro Leu Ala Pro Cys Ser Arg Ser Thr Ser Glu Ser Thr Ala Ala Leu
130                 135                 140 ggc tgc ctg gtc aag gac tac ttc gcc gaa                             462
Gly Cys Leu Val Lys Asp Tyr Phe Ala Glu
145                 150

<210> SEQ ID NO 2
<211> LENGTH: 154
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro His Tyr Thr Arg Gly Phe Asp Tyr Trp Gly Lys Gly
            100                 105                 110

Thr Leu Val Thr Val Ser Ser Ala Ser Thr Lys Gly Pro Ile Gly Leu
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Ala Glu
145                 150

<210> SEQ ID NO 3
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 3 gat gtt gtg atg acc cag act cca ctc tct ctg tcc gtc acc cct gga     48
Asp Val Val Met Thr Gln Thr Pro Leu Ser Leu Ser Val Thr Pro Gly
1               5                   10                  15 cag ccg gcc tcc atc tcc tgc agg tct agt cag agc ctc ctg cat agt     96
Gln Pro Ala Ser Ile Ser Cys Arg Ser Ser Gln Ser Leu Leu His Ser
            20                  25                  30 gat gga atg acc tat ttt tct tgg tat ttg cag aag cca ggc cag cct     144
Asp Gly Met Thr Tyr Phe Ser Trp Tyr Leu Gln Lys Pro Gly Gln Pro
        35                  40                  45 cca cag ctc ctg atc tat gaa gtt tcc aac cgg ttc tct gga gtg cca     192
```

```
Pro Gln Leu Leu Ile Tyr Glu Val Ser Asn Arg Phe Ser Gly Val Pro
    50                  55                  60 gat agg ttc agt ggc agc ggg tca ggg aca gat ttc aca ctg aaa atc        240
Asp Arg Phe Ser Gly Ser Gly Ser Gly Thr Asp Phe Thr Leu Lys Ile
65                  70                  75                  80 agc cgg gtg gag gct gag gat gtt ggg gtt tat tac tgc atg caa aat        288
Ser Arg Val Glu Ala Glu Asp Val Gly Val Tyr Tyr Cys Met Gln Asn
                85                  90                  95 ata cag ctt ccg tgg acg ttc ggc caa ggg acc aag gtg gaa atc aaa        336
Ile Gln Leu Pro Trp Thr Phe Gly Gln Gly Thr Lys Val Glu Ile Lys
                100                 105                 110 cga act gtg gct gca cca tct gtc ttc atc ttc ccg cca tct gat            381
Arg Thr Val Ala Ala Pro Ser Val Phe Ile Phe Pro Pro Ser Asp
        115                 120                 125

<210> SEQ ID NO 4
<211> LENGTH: 127
<212> TYPE: PRT
<213> ORGANISM: Homo sapiens

<400> SEQUENCE: 4

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
                20                  25                  30

Asp Gly Met Thr Tyr Phe Ser Trp Tyr Leu Gln Lys Pro Gly Gln Pro
            35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asn
                85                  90                  95

Ile Gln Leu Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp
        115                 120                 125
```